United States Patent
Dorn et al.

(10) Patent No.: US 9,020,304 B2
(45) Date of Patent: Apr. 28, 2015

(54) METHOD FOR LOADING MEDICAL IMAGE DATA AND DEVICE FOR PERFORMING THE METHOD

(71) Applicant: Siemens Aktiengesellschaft, Munich (DE)

(72) Inventors: Karlheinz Dorn, Kalchreuth (DE); Helmut König, Erlangen (DE); Vladyslav Ukis, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 108 days.

(21) Appl. No.: 13/773,781

(22) Filed: Feb. 22, 2013

(65) Prior Publication Data

US 2013/0266242 A1     Oct. 10, 2013

(30) Foreign Application Priority Data

Apr. 5, 2012   (EP) .................................... 12163393

(51) Int. Cl.
  *G06K 9/54*   (2006.01)
  *G06K 9/00*   (2006.01)
  *G06T 1/60*   (2006.01)
  *G06F 19/00*  (2011.01)

(52) U.S. Cl.
  CPC ......... *G06T 1/60* (2013.01); *G06T 2207/10081* (2013.01); *G06T 2207/10088* (2013.01); *G06F 19/321* (2013.01)

(58) Field of Classification Search
  CPC ............ G06T 1/60; G06T 2207/10088; G06T 2207/10081; G06T 2207/10016; G06F 19/321; G06Q 50/24
  USPC .................. 382/128–134, 305, 312; 707/602
  See application file for complete search history.

(56) References Cited

U.S. PATENT DOCUMENTS

| 7,421,136 B2 * | 9/2008 | Sirohey et al. ................ 382/240 |
| 7,844,571 B2 * | 11/2010 | Konig ............................ 707/602 |
| 7,974,924 B2 * | 7/2011 | Holla et al. ..................... 705/51 |
| 2009/0003270 A1 | 1/2009 | Schwenke |
| 2009/0132636 A1 | 5/2009 | Natanzon et al. |

FOREIGN PATENT DOCUMENTS

WO    WO 9916250 A1    4/1999

OTHER PUBLICATIONS

European Priority Document EP12163393.7 filed Apr. 5, 2012.

* cited by examiner

*Primary Examiner* — Kanjibhai Patel
(74) *Attorney, Agent, or Firm* — Harness, Dickey & Pierce, P.L.C.

(57) ABSTRACT

In order to enable improved or even optimized loading of medical image data, a data type representing the image data is determined in at least one embodiment from the image data in a first step and a data-type-specific default loading strategy is selected according to the data type. The default loading strategy may be refined, in at least one example embodiment, to produce a loading strategy based on additional context data. The context data is obtained for example during an initial assessment of the image data. For this purpose, provision is made in particular for a shared index to be generated in which the context data is stored together with further information associated with the image data of a plurality of objects that are to be examined.

20 Claims, 2 Drawing Sheets

METHOD FOR LOADING MEDICAL IMAGE DATA AND DEVICE FOR PERFORMING THE METHOD

PRIORITY STATEMENT

The present application hereby claims priority under 35 U.S.C. §119 to European patent application number EP 12163393 filed Apr. 5, 2012, the entire contents of which are hereby incorporated herein by reference.

FIELD

At least one embodiment of the invention generally relates to a method for loading medical image data in order to make said data available to an image processing program, the image data having been generated from raw data of a medical imaging system during the scanning of an object and the image data associated with a respective object in each case comprising metadata and pixel data. At least one embodiment of the invention further generally relates to a device for performing such a method.

BACKGROUND

Medical image data can originate from the most disparate image-generating devices, referred to as modalities. Modalities of this type include for example computed tomography scanners, magnetic resonance tomography systems, simple x-ray machines for generating projection images, etc. Image data from various modalities may be available in relation to a patient. The image data is stored in a shared image processing system (PACS) within a clinical environment for example. For processing purposes the image data from said image storage system is displayed or loaded for image processing and image evaluation at the request of a particular local client computer. The corresponding image processing program (application) is normally installed on a powerful server. In this scenario different applications are available for image processing purposes and are selected accordingly as a function of the requirements.

The image data is typically stored in accordance with the so-called DICOM standard (DICOM=Digital Imaging and Communications in Medicine). The image data comprises META data, which conceptually represents an element called the "header", and the actual image data containing the image information as pixel data.

As a result of the increasingly higher resolution of present-day digital image-generating devices the image data of an examined object is on occasion—depending on modality—very extensive, with a storage requirement of several gigabytes.

These large data volumes result in a deterioration in performance during the loading of the data, for example into a working memory of the server which the image processing program accesses in order to evaluate and analyze the image data. This leads in some cases to acceptance problems on the part of the medical personnel as users of applications of said type.

US 2009/0132636 A1 discloses a method in which so-called loading plans are provided for a delivery chain in order to deliver the data to different points, wherein for example in the event of multiple requests from different client computers the data is routed via suitable data node points taking into account data bottlenecks.

SUMMARY

A method and a device are disclosed which, in at least one embodiment, enable the image data to be loaded faster and in an improved manner from a central image data memory into a working memory.

In the method for loading medical image data of at least one embodiment, the image data is assigned to a data type and subsequently a loading strategy assigned to the determined data type is selected from a plurality of data-type-specific loading strategies and utilized for loading the image data so that the data will be available for the image processing program (application). In this case the image data has generally been generated from raw data of a medical imaging system during the scanning of an object. The object is in particular a specific region of a patient's body, a specific organ or else, in pathological findings, a tissue sample. According to the DICOM standard the image data is in this case stored in a central data memory in particular within a PACS system. Accordingly, the image data also includes metadata as well as pixel data containing the actual image information.

BRIEF DESCRIPTION OF THE DRAWINGS

An example embodiment of the invention is explained in more detail below with reference to the figures, in which.

DETAILED DESCRIPTION OF THE EXAMPLE EMBODIMENTS

Figure 1:
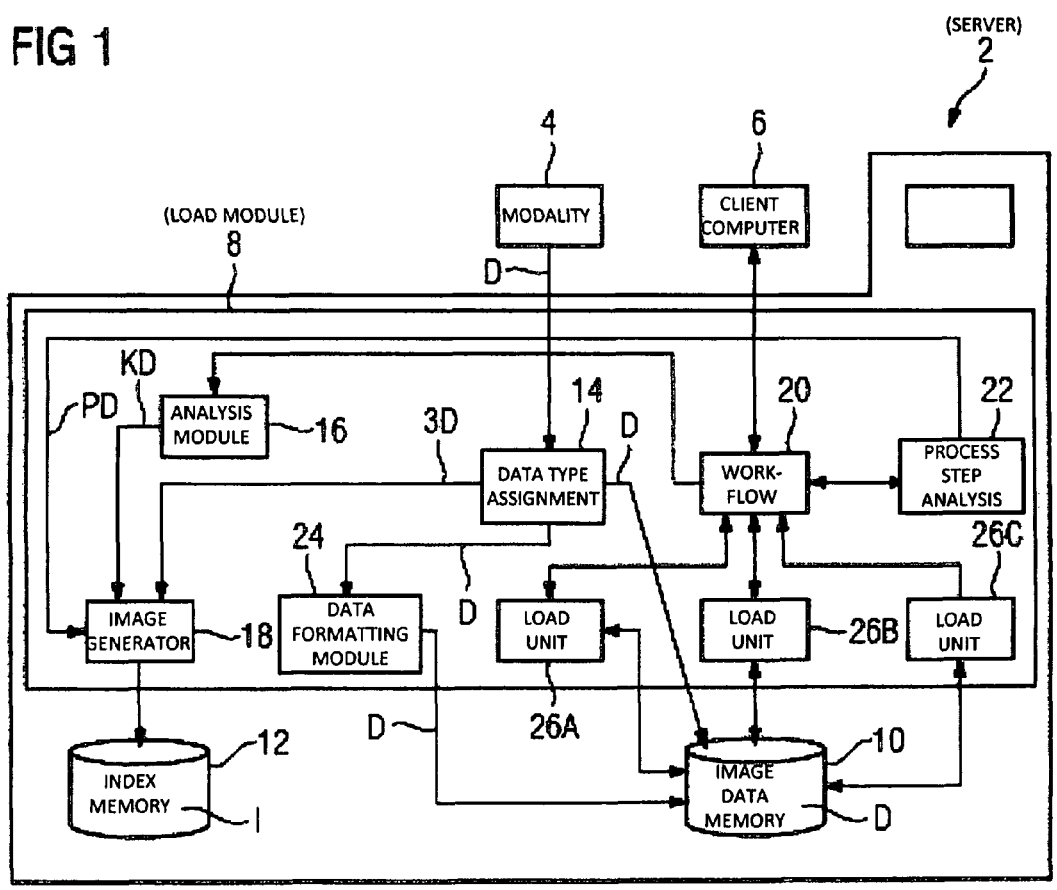
FIG. 1 shows in the form of a block diagram a medical image data processing system with the aid of which the method for loading medical image data will be explained in more detail.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the method for loading medical image data of at least one embodiment, the image data is assigned to a data type and subsequently a loading strategy assigned to the determined data type is selected from a plurality of data-type-specific loading strategies and utilized for loading the image data so that the data will be available for the image processing program (application). In this case the image data has generally been generated from raw data of a medical imaging system during the scanning of an object. The object is in particular a specific region of a patient's body, a specific organ or else, in pathological findings, a tissue sample. According to the DICOM standard the image data is in this case stored in a central data memory in particular within a PACS system. Accordingly, the image data also includes metadata as well as pixel data containing the actual image information.

By different "data types" of the image data is to be understood a different data structure of the image data. Depending on modality and requirement, the raw data is usually stored in different data structures conforming to the DICOM standard.

By way of at least one embodiment of the method an analysis is now carried out in a first step to determine the data type, i.e. the data structure, of the image data. A loading strategy tailored to this particular data type is subsequently selected and is then used for loading the image data into a working memory in order to make the data available for the image processing. Performance-improved or even optimized loading is made possible by way of this data-type-specific loading strategy.

The method is performed here with the aid of a load module which is preferably stored on a server, in particular a multimodality server. By multimodality server is to be understood a server which processes image files originating from different modalities. Basically, the image data can be stored on said server or alternatively at a remote storage location. Firstly, the data type is identified automatically with the aid of the load module, which is in the form of a software component, and then a data type is assigned to the image data of the respective object with the aid of a data type assignment module. Finally, the load module additionally contains a sequencing or workflow module via which the image data loading operation is controlled. The workflow module in particular selects the default loading strategy provided for the respective data type from predefined default loading strategies.

The data types and data structures of the image data can be assigned in particular to the following groups:
a) volume image data based on acquisitions of individual slices, such as is generated for example in the course of a computed tomography examination or in the course of a magnetic resonance imaging examination;
b) volume image data based on multiframe image data; this is data stored in accordance with a special DICOM standard. With this, for example, the image data of multiple slice images having shared attributes which are combined in a shared header is combined in a so-called "multiframe".
c) image data conforming to the WSI standard within the DICOM standard (WSI=Whole Slide Imaging). This is a standard developed in particular for images generated during digital microscopy, for pathological applications for example. In said WSI image data the data is usually stored in structures called tile pyramids, in particular with z-stacks which are optional for the highest image resolution. In said tile pyramids the image data having different resolutions is stored in different "planes" of the pyramid. In this scheme the base of the pyramid defines image data having the highest resolution. In addition each plane of the pyramid is subdivided into individual fields, called tiles.

d) projection image data, as obtained in particular in a traditional x-ray examination such as radiography for example.

The image data corresponding to the data types is fundamentally different both in terms of its structure and in terms of its data volume, so that a different loading strategy for each of the types, in other words a different algorithm for loading the images from the image data memory, leads to an optimization of the loading time. Thus, it is provided in the case of the WSI data for example that not all of the data is loaded simultaneously, but that data from a predefined plane having a predefined resolution is loaded. In the case of the volume image data according to the data types a) and b), for example, image data from the middle of the image dataset representing the center of the image is loaded according to the default loading strategy, since this is where the regions of interest are presumed to be. In the case of the simple projection images according to data type d), finally, the default loading strategy can consist in immediately loading the complete dataset in its entirety, because the image data volumes here are very small compared to the other data types.

In a example embodiment, the data type is determined in this case on the basis of the metadata contained in the image data. The data type assignment module therefore analyzes the metadata in order to assign the image data to a specific data type. This is because according to the DICOM standard the metadata includes information permitting inferences to be made concerning the modality and hence the respective data type. In particular the data type is categorized and assigned using the DICOM attribute "SOP Class UID" (SOP=Service Object Pair; UID=United Identifier). By this means, therefore, information already present in the actual image data is evaluated in an effective manner.

In a particularly example embodiment, additional context data is assigned to the image data along with the metadata, with the default loading strategy being specified in addition on the basis of the context data and a modified loading strategy being determined. The default loading strategy previously identified via the data type is therefore specified in finer detail with the aid of the context data. The context data is supplementary information that is not contained in the metadata. The evaluation of said additional context information therefore yields additional information which is taken into account in order to achieve an optimal loading result.

In order to realize this it is furthermore provided in a beneficial embodiment to generate a shared index for a plurality of medical objects. Preferably the index comprises all, or at least a major part of, the image data(sets) stored in the database in relation to the respective objects. The context data associated with a particular object is assigned to the image data of said object via the index. This shared index, which is generated in particular by the load module, is accessed by the load module preferably when a request is made, i.e. during a loading operation, in order to determine the modified loading strategy therefrom.

In this case the index is beneficially stored in a separate dedicated index data memory. The index for the image data of a respective object is beneficially generated as soon as the image data is transmitted by an imaging medical device to the server on which the load module is installed. Usually, therefore, the index is generated independently of a specific loading operation for making the image data available for an image processing program. For this purpose an index generator for generating the index is provided within the load module. In this case all the information that is relevant for determining a performance-improved or even optimized loading strategy is stored in the index for example in the manner of a table structure assigned to the respective object. Also stored in the index in addition to the identification of the storage location of the image data for example is relevant information from the metadata, such as e.g. information about the modality, date of the scan, organ that is to be examined, etc. In addition different types of context data are written into the index. If said context data is not (yet) available when the image data is first acquired, the corresponding fields in the index initially remain empty, but are then filled automatically as soon as the corresponding information is present.

Information from an already completed, preceding analysis and evaluation of the image data is stored as a first group of context information. For this purpose the load module beneficially includes an analysis module which is embodied for automatically extracting context data from the results of the preceding evaluation.

This group of context data comprises in particular information concerning relevant imaging areas, called the "region of interest" (ROI). The region of interest is identified for example in a preceding evaluation as part of an—in particular automatic—segmentation method. The modified loading strategy accordingly provides to preload such previously identified imaging regions before the remaining data of the image dataset is read in. By means of this measure the relevant imaging region is therefore immediately presented for viewing to the medical personnel, thereby enabling the data to be processed immediately. A significant performance optimization is achieved in this way. If a plurality of imaging regions are classified as regions of interest in the course of a preceding evaluation/assessment, for example within the scope of main findings and secondary findings, then these are loaded in succession according to a predefined weighting, based for example on the classification as main findings and secondary findings.

Beneficially, the image loading strategy is additionally determined taking into account the object that is to be examined, i.e. in particular on an organ-specific basis. For this purpose recourse is made once again in particular to data of the index, for example the context data. This affords the possibility for example of initially loading only the image data that is relevant to the respective organ of interest. If the anatomical region of interest is a bone structure, for example, the modified loading strategy is applied for loading only such data which comes into consideration at all on the basis of its structure, such as grayscale values for example.

Finally, objectives of the examination, the so-called "reason for study", are also evaluated in order to determine the modified loading strategy. This embodiment is based on the consideration of initially loading such data that may most likely contain information for the examination objective.

In addition an analysis of the workflows provided for the image processing is also preferably performed by the load module. In this case even while a first work step is being executed the next work step is already determined and the data relevant to the work step is preloaded. The data is therefore loaded successively in accordance with the modified loading strategy as a function of the sequence of the workflows.

To sum up, the improved or even optimized loading strategy and consequently the load module are therefore configured with the aim of selectively evaluating a plurality of information from the metadata and from the context data as well as from the analysis of workflows/process steps in order to identify from the comprehensive image data of a particular object the image data that is relevant for the image processing and initially to load said data in a targeted manner in order to enable the image data to be processed immediately insofar as is possible.

A significant consideration in this scenario is the generation of the index, which preferably contains all of the relevant information for determining the modified loading strategy, namely in particular the metadata and the context data associated with the image data of a plurality of examined objects. In order to determine the modified, performance-improved or even optimized loading strategy the load module beneficially refers solely to the information stored in the index.

The medical system shown in FIG. 1 is for example part of a hospital image data system or constitutes the same. The system includes a server 2 for processing image data D which preferably originates from different medical imaging units, referred to as modalities 4. Preferably a plurality of individual client computers 6 are connected to the server 2. Only one modality 4 and one client computer 6 are shown in the figure for illustration purposes.

A load module 8 is installed on the server 2 as an executable software program by way of which the loading of image data D described here is controlled. The server 2 additionally includes an image data memory 10 in which image data D of various objects examined by means of the modalities 4 is stored. Finally, the server 2 also includes an index memory 12 in which an index I is stored. Both the image data memory 10 and the index memory 12 can be implemented in hardware separately from the server 2 and be connected thereto via a data line.

The load module 8 is in turn subdivided into multiple functional modules. These are
a data type assignment module 14 with the aid of which a data type is assigned to the image data D of a respective object,
an analysis module 16,
an index generator 18,
a workflow module 20,
a process step analysis module 22,
a data formatting module 24, and
a number of load units 26A to 26C.

The image data D is transmitted to the load module 8 by the modality 4. The image data D generally includes pixel data P and metadata M, which constitutes an element called the "header". The data type assignment module 14 analyzes the metadata M and on the basis of the information contained therein assigns the image data D to a specific data type A1 . . . A4 (cf. FIG. 2). The assignment module 14 transmits index data ID to the index generator 18 together with further information extracted from the image data D.

Figure 2:
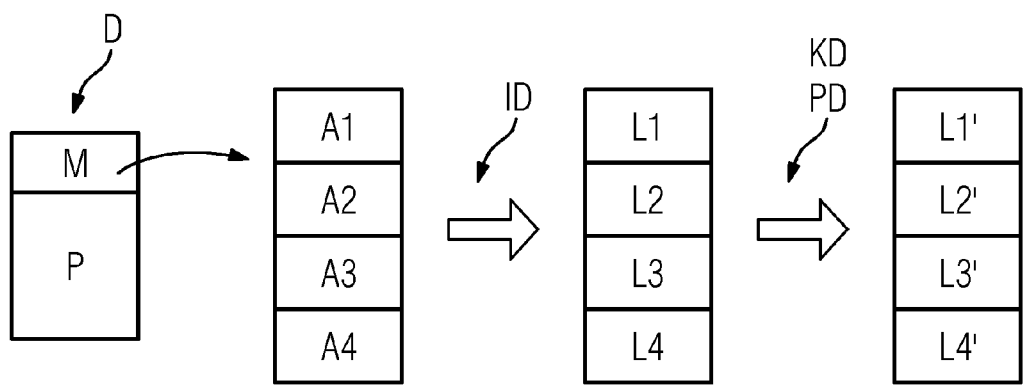
FIG. 2 is a simplified schematic diagram to illustrate how a modified loading strategy is determined.

As is also apparent from FIG. 2, each data type A1 . . . A4 is assigned a respective default loading strategy L1 . . . L4.

The image data received from the modality 4 is forwarded by the assignment module 14 to the image data memory 10 for storage therein.

In the event that the image data D is not yet present in a desired, standardized format, provision is made for the image data D to be forwarded to the data formatting module 24, in which the image data D is converted into a desired format. This relates in particular to the conversion into the WSI format with the tile-pyramid-shaped data structure conforming to the DICOM standard, insofar as the data is not yet available in said format and if the image data D has been assigned to the data type A3.

On the basis of the index data ID, an index I is generated with the aid of the index generator 18 or an already existing index is incremented. Said index I is essentially an assignment table from which various information is indexed and hence assigned to a respective image dataset associated with an object. In particular all the information that is useful or necessary for determining a modified loading strategy L1' . . . L4', as well as information concerning the storage location of the image data, etc., is stored in said index table.

The index generator 18 additionally receives context data KD from the analysis module 16. The analysis module 16 is a postprocessing analysis module which evaluates the results of a preceding evaluation of the image data D and extracts relevant data therefrom. Thus, for example, an imaging region of interest (ROI) has already been identified in the image data D either automatically or by the medical personnel in the course of a first analysis (assessment). The analysis module 16 evaluates the initial findings and from these determines context data KD, for example the identification of the data segments which show the ROI. Said context data KD is stored in the index table as soon as it becomes available. The index is preferably supplemented continuously and updated in the course of subsequent examinations. In particular information relating to main findings and secondary findings is also extracted by way of the analysis module 18 and transmitted to the index generator 18. The default loading strategy L1 . . . L4 is improved with the aid of said context data KD and a modified loading strategy L1' . . . L4' is determined, as illustrated in simplified form in FIG. 2.

The image data D is processed or evaluated with the aid of an image processing program (application) on the server 2 usually at the request of a client computer 6. A corresponding request is submitted by the image processing program (application) to the workflow module 20 in order to load the required image data D in particular into a working memory. The workflow module 20 accesses the index memory 12 (not shown in further detail in the figure) and from the information contained in the index I determines a modified loading strategy L1' . . . L4' for loading the desired image data D from the image data memory 10.

In this case one of the default loading strategies L1 . . . L4 is preferably selected in a first step on the basis of the data type, each default loading strategy L1 . . . L4 being assigned one of the load units 26A to 26C (only three load units 26A to 26C are shown in FIG. 1 by way of example). The predefined default loading strategy is refined and improved on the basis of the further information contained in the index I, in particular the context data KD. The image data D is then loaded via the load unit 26A to 26C selected according to the data type A1 . . . A4 in accordance with said refined, modified loading strategy L1' . . . L4' and transmitted to the client computer 6.

In the example embodiment, the results of the analysis of the image data D performed either automatically or manually by means of the image processing program are made available via the workflow module 20 to the analysis module 16, which immediately analyzes the performed evaluation of the image data D and extracts relevant data as context data KD and transmits the data to the index generator 18.

The evaluation programs typically execute a defined sequence of work steps. Said defined sequence is defined for example by a separate evaluation manager (which is not shown in further detail here). The sequence of said individual work steps is analyzed and evaluated via the process step analysis module 22. The result of the evaluation is in turn transmitted to the workflow module 22, such that in particular during the execution of a work step N the data for the following work step N+1 is already being loaded in the background.

A predefined sequence of work steps is often not executed completely within a working session. In order to allow for this the process step analysis module 22 transmits process data PD containing information about the application applied to the image data D and the most recently performed application step to the index generator 18. The data is also entered into the index as further context data KD and taken into account by the workflow module 20 at the time of the next load request for the purpose of determining a modified loading algorithm L1' . . . L4'.

The improved method for loading image data D described here is characterized in that an improvement in the performance of the server 2 and consequently also of all the applications/image processing programs executing thereon is achieved. This is realized on the one hand through the application of a default loading strategy L1 . . . L4 specifically tailored to the respective data type and represented by a special loading algorithm. A significant aspect is furthermore to be seen in the fact that said default loading strategy is specified by way of context data KD and a modified loading strategy L1' . . . L4' is determined. The identification of an imaging region of interest (ROI) is important in this, so that a relevant region of interest is always the first thing displayed to the physician during a postprocessing operation. A quantitative evaluation of the lung density can be referred to as an example. This is based on what is termed a thorax CT study. Whereas currently, in the absence of a special loading strategy, the study is presented to the physician in unsegmented form in a standard layout, by means of the method described here having the improved or even optimized loading strategy the physician is presented first with a 3D visualization of the segmented lung. This is achieved in that the region of interest (ROI lung) is entered in the shared index I and is loaded first.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims.

Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method comprising:
loading medical image data to make the image data available to an image processing program, the image data having been generated from raw data obtained by a medical imaging system during scanning of an object, and the image data including metadata and pixel data associated with the object, the loading including,
assigning the image data to a data type out of a plurality of possible data types,
subsequently selecting, out of a plurality of data-type-specific loading strategies, a loading strategy assigned to the data type, and
utilizing the selected loading strategy for loading the image data.

2. The method of claim 1, wherein the plurality of possible data types include:
volume image data based on individual slice images as a first data type,
volume image data based on multiframe image data as a second data type,
image data conforming to a whole slide imaging standard within a DICOM standard as a third data type, and
projection image data as a fourth data type.

3. The method of claim 1, wherein the data type is assigned on the basis of the metadata.

4. The method of claim 1, wherein the image data is additionally assigned context data and the loading strategy is selected based on the context data.

5. The method of claim 4, wherein a shared index is generated for the image data of a plurality of medical objects, in which index associated context data is assigned to the image data of a respective object, the index being accessed in order to determine the context data.

6. The method of claim 5, wherein the loading strategy is determined based on information stored in the index.

7. The method of claim 5, wherein the data type is assigned and an entry made in the index as soon as the image data is received from an imaging medical device.

8. The method of claim 4, wherein information from a preceding evaluation of the image data is stored in the context data.

9. The method of claim 4, wherein the loading strategy is selected taking into account information relating to imaging regions of interest which were identified in a preceding assessment.

10. The method of claim 9, wherein a plurality of imaging regions are identified these are loaded in succession according to a weighting.

11. The method of claim 4, wherein the loading strategy is selected taking into account the type of object that is to be examined.

12. The method of claim 4, wherein the loading strategy is selected taking into account examination objectives.

13. The method of claim 1, wherein workflows predefined for image processing on the image processing program are stored and the loading strategy is selected by the sequence of the workflows.

14. A device comprising:
- a computer unit including a processor and a memory, the processor having a load module to load medical image data to make the image data available to an image processing program, the image data having been generated from raw data obtained by a medical imaging system during scanning of an object, and the image data including metadata and pixel data associated with the object, the load module being further configured to,
  - assign the image data to a data type from among a plurality of possible data types,
  - subsequently select, from among a plurality of data-type-specific loading strategies, a loading strategy assigned to the data type, and
  - utilize the selected loading strategy for loading the image data.

15. The device of claim 14, wherein the load module comprises:
- a data type assignment module for assigning the data type to the image data,
- an index generator for generating an index,
- an analysis module for automatically extracting context data from a preceding evaluation of the image data, and
- a workflow module for controlling the loading of the image data and determining, based on information stored in the index, the loading strategy for loading the image data from an image data memory.

16. The method of claim 2, wherein the data type is assigned based on the metadata.

17. The method of claim 6, wherein the data type is assigned and an entry made in the index in response to receiving the image data from an imaging medical device.

18. A device comprising:
- a computer unit including a processor and a memory, the processor having a load module configured to load medical image data to make the image data available to an image processing program, the image data having been generated from raw data obtained by a medical imaging system during scanning of an object, and the image data including metadata and pixel data associated with the object, the load module being further configured to,
  - assign the image data to a data type from among a plurality of possible data types,
  - subsequently select, from among a plurality of data-type-specific loading strategies, a loading strategy assigned to the data type, and
  - utilize the selected loading strategy for loading the image data, wherein
    - the image data is additionally assigned context data and the loading strategy is selected based on the context data.

19. A non-transitory computer readable medium including program segments for, when executed on a computer device, causing the computer device to implement the method of claim 1.

20. A non-transitory computer readable medium including program segments for, when executed on a computer device, causing the computer device to implement the method of claim 4.

* * * * *